US010400548B2

(12) United States Patent
Wong et al.

(10) Patent No.: US 10,400,548 B2
(45) Date of Patent: Sep. 3, 2019

(54) SHARED EQUATION OF STATE CHARACTERIZATION OF MULTIPLE FLUIDS

(71) Applicant: Landmark Graphics Corporation, Houston, TX (US)

(72) Inventors: Terry Wong, Houston, TX (US); Graham Fleming, Houston, TX (US)

(73) Assignee: Landmark Graphics Corporation, Houston, TX (US)

( * ) Notice: Subject to any disclaimer, the term of this patent is extended or adjusted under 35 U.S.C. 154(b) by 331 days.

(21) Appl. No.: 15/116,189

(22) PCT Filed: Mar. 12, 2015

(86) PCT No.: PCT/US2015/020299
§ 371 (c)(1),
(2) Date: Aug. 2, 2016

(87) PCT Pub. No.: WO2015/138811
PCT Pub. Date: Sep. 17, 2015

(65) Prior Publication Data

US 2017/0009558 A1 Jan. 12, 2017

Related U.S. Application Data

(60) Provisional application No. 61/951,831, filed on Mar. 12, 2014.

(51) Int. Cl.
*E21B 41/00* (2006.01)
*E21B 43/00* (2006.01)
(Continued)

(52) U.S. Cl.
CPC .......... *E21B 41/0092* (2013.01); *E21B 43/00* (2013.01); *E21B 43/122* (2013.01);
(Continued)

(58) Field of Classification Search
CPC ...... G06F 17/5018; G06F 17/16; G06F 17/11; G06F 2217/16; G01F 1/74; G05B 17/02;
(Continued)

(56) References Cited

U.S. PATENT DOCUMENTS 6,108,608 A 8/2000 Watts, III
2007/0112547 A1 5/2007 Ghorayeb et al.
(Continued)

FOREIGN PATENT DOCUMENTS

WO WO-2013188087 A1 12/2013

OTHER PUBLICATIONS

Reyadh A. Almehaideb et al, "EOS tuning to model full field crude oil properties using multiple well fluid PVT analysis", 2000, Journal of Petroleum Science and Engineering, vol. 26, Issues 1-4, pp. 291-300.*

(Continued)

*Primary Examiner* — Juan C Ochoa

(57) ABSTRACT

System and methods of modeling fluids in a simulation of fluid production in a multi-reservoir system with a common surface network are provided. Pressure-volume-temperature (PVT) data is determined for fluids in each of a plurality of reservoirs coupled to the common surface network. A shared equation of state (EOS) characterization representing each of the fluids across the plurality of reservoirs is generated based on the corresponding PVT data. Data representing properties of the fluids in each reservoir is calculated based on the shared EOS characterization of the fluids. When the calculated data is determined not to match the PVT data associated with the fluids in each reservoir, to the shared EOS characterization is adjusted based on a difference between the calculated data and the PVT data.

20 Claims, 5 Drawing Sheets

400
402 Determine PVT data for multiple fluids in desired pressure and temperature ranges within common surface network
404 Define common set of light components for all fluids across plurality of reservoirs
406 Define C7+ characterization for fluids in each reservoir
408 Adjust C7+ characterization of fluids in each reservoir to match corresponding PVT data from step 402
410 Determine common set of components for C7+ fraction and apply mixing rules to determine composition and properties of common components
412 Attempt to match PVT data with new characterization and calculate interaction coefficients for component differences between characterizations
414 Is Match Satisfactory?
NO
YES
416 Finalize characterization

(51) Int. Cl.
*E21B 43/12* (2006.01)
*E21B 47/06* (2012.01)
*E21B 49/08* (2006.01)
*G01N 33/28* (2006.01)
*G05B 17/02* (2006.01)
*G06F 17/50* (2006.01)

(52) U.S. Cl.
CPC ............ *E21B 47/06* (2013.01); *E21B 47/065* (2013.01); *E21B 49/08* (2013.01); *G05B 17/02* (2013.01); *G06F 17/5009* (2013.01); *G01N 33/2823* (2013.01)

(58) Field of Classification Search
CPC ...... E21B 41/0092; E21B 43/14; E21B 47/10; E21B 49/08; E21B 47/06; E21B 47/065
USPC ........................................................ 703/10, 2
See application file for complete search history.

(56) References Cited

U.S. PATENT DOCUMENTS

2009/0192768 A1 7/2009 Zuo et al.
2009/0288881 A1 11/2009 Mullins et al.
2013/0197808 A1* 8/2013 Zuo ......................... E21B 47/00 702/6

OTHER PUBLICATIONS

Fleming and Wong, "Fully Coupled Simulation of Multiple Compositional Reservoirs With a Shared Facility Network", 2013, SPE Reservoir Simulation Symposium, Society of Petroleum Engineers, pp. 1-19.*

International Search Report and Written Opinion, dated Nov. 24, 2015, 10 pages; Korean International Searching Authority.

Curtis H. Whitson, Characterizing Hydrocarbon Plus Fractions, Oct. 21-24, 1980, pp. 683-694, SPE12233, Society of Petroleum Engineers, 1980 European Offshore Petroleum Conference and Exhibition, London.

Karen Schou Pedersen, Ann Lisbeth Blilie and Knut Kristian Meisingset, PVT Calculations on Petroleum Reservoir Fluids Using Measured and Estimated Compositional Data for the Plus Fraction, 1992, pp. 1378-1384 , Ind. Eng. Chem. Res., vol. 31, No. 5 American Chemical Society.

Curtis H. Whitson, Thomas F. Anderson and Ingolf Søreide, C7+ Characterization of Related Equilibrium Fluids Using the Gamma Distribution, 1989, Chorn, L.G. and Mansoori, G.A., CRC Press, New York.

Curtis H. Whitson, Some Aspects of Phase Behavior in Reservoir Simulation, Jul. 23-27, 1990, 56 Pages, Third International Forum on Reservoir Simulation, Baden, Austria.

* cited by examiner

SHARED EQUATION OF STATE CHARACTERIZATION OF MULTIPLE FLUIDS

CROSS-REFERENCE TO RELATED APPLICATIONS

The present application is a U.S. National Stage patent application of International Patent Application No. PCT/US2015/020299, filed on Mar. 12, 2015, which claims the benefit of U.S. Provisional Patent Application No. 61/951,831, filed on Mar. 12, 2014, titled “Procedure for Shared Equation of State Characterization of Multiple Fluids,” the benefit of both of which are claimed and the disclosure of both of which are incorporated herein by reference in their entireties.

FIELD OF THE DISCLOSURE

The present disclosure relates generally to the recovery of subterranean deposits and to more specifically to the recovery of subterranean hydrocarbon deposits from multiple reservoirs through a common surface network.

BACKGROUND

When multiple reservoirs are produced through a common facility network, the capability to integrate the modeling of surface and subsurface can be critical to field development and optimization. The shared facility network imposes constraints that the combined production cannot exceed, determines the pressure drop in the flow lines, and the composition and volume of the sales and reinjection streams. Pressure drop in flow lines is particularly important in deepwater field development, where flow lines are long, and production from multiple reservoirs can flow through the same riser.

Often, the fluid characterizations of these reservoirs have been derived independently. In each case, the appropriate fluid representation was selected that provided an optimum combination of accuracy and computational efficiency. The two most common fluid characterizations are the equation of state (EOS) model and the black oil model.

A hydrocarbon fluid may actually be composed of hundreds of distinct components. When modeling using an EOS, the engineer must specify the number of pseudo-components (typically 5 to 12) and their EOS properties. Pseudo-components are combinations of actual components. Alternatively, black-oil modeling involves specification of a number of common engineering measurements in tables that vary with pressure. However, it is inherently a model with two pseudo-components. The net result is that the different connected reservoirs are being modeled with a variable number of pseudo-components, some of which may be common. However, even the common pseudo-components may have different fluid properties in the different reservoirs.

While a myriad of papers have been written about matching a single fluid, almost none have been devoted to matching a set of fluids. In most cases, the authors have tried to match multiple fluids with a single EOS model. In rare cases, they have matched the fluids with the same component set, but allowed the components to have different properties. For example, one popular approach is to have the fluids have the same components and the same properties, but different amounts of each component. However, this approach is useful only when the fluids are related in some way, for example, fluids in a gas cap or associated oil rim within the same petroleum reservoir.

BRIEF DESCRIPTION OF THE DRAWINGS

Illustrative embodiments of the present disclosure are described in detail below with reference to the attached drawing figures.

Figures 1A, 1B:
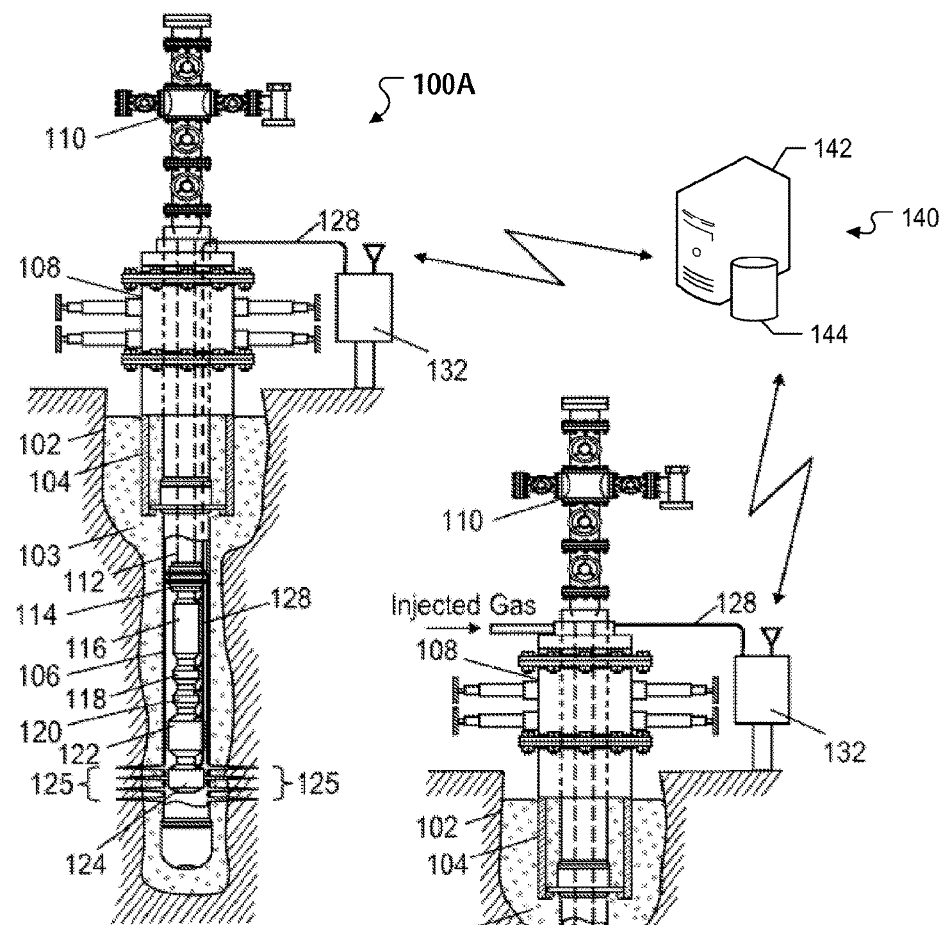
FIGS. 1A and 1B illustrate examples of production wells suitable for hydrocarbon production and exploration from a subsurface reservoir.

The illustrated figures are only exemplary and are not intended to assert or imply any limitation with regard to the environment, architecture, design, or process in which different embodiments may be implemented.

DESCRIPTION OF ILLUSTRATIVE EMBODIMENTS

Embodiments of the present disclosure relate to using a shared equation of state (EOS) characterization of multiple fluids to simulate fluid production in a multi-reservoir system with a common surface network. While the present disclosure is described herein with reference to illustrative embodiments for particular applications, it should be understood that embodiments are not limited thereto. The description of the present disclosure has been presented for purposes of illustration and description, but is not intended to be exhaustive or limited to the embodiments in the form disclosed. Many modifications and variations will be apparent to those of ordinary skill in the art without departing from the scope and spirit of the disclosure. The illustrative embodiments described herein are provided to explain the principles of the disclosure and the practical application thereof, and to enable others of ordinary skill in the art to understand that the disclosed embodiments may be modified as desired for a particular implementation or use. The scope of the claims is intended to broadly cover the disclosed embodiments and any such modification. Any actual data values listed in the detailed description are provided for illustrative purposes only and embodiments of the present disclosure are not intended to be limited thereto. Thus, the operational behavior of embodiments will be described with the understanding that modifications and variations of the embodiments are possible, given the level of detail presented herein.

In the detailed description herein, references to “one embodiment,” “an embodiment,” “an example embodiment,” etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

As used herein, the singular forms "a", "an" and "the" are intended to include the plural forms as well, unless the context clearly indicates otherwise. It will be further understood that the terms "comprise" and/or "comprising," when used in this specification and/or the claims, specify the presence of stated features, integers, steps, operations, elements, and/or components, but do not preclude the presence or addition of one or more other features, integers, steps, operations, elements, components, and/or groups thereof. The corresponding structures, materials, acts, and equivalents of all means or step plus function elements in the claims below are intended to include any structure, material, or act for performing the function in combination with other claimed elements as specifically claimed.

The disclosed embodiments and advantages thereof are best understood by referring to the drawings, in which like numerals are used for like and corresponding parts of the various drawings. Other features and advantages of the disclosed embodiments will be or will become apparent to one of ordinary skill in the art upon examination of the following figures and detailed description. It is intended that all such additional features and advantages be included within the scope of the disclosed embodiments. Further, the illustrated figures are only exemplary and are not intended to assert or imply any limitation with regard to the environment, architecture, design, or process in which different is embodiments may be implemented.

As noted above, the disclosed embodiments relate to using a shared EOS characterization of multiple fluids during a simulation of fluid production in a multi-reservoir system with a common surface network. As will be described in further detail below, reservoir fluids from multiple hydrocarbon reservoirs may be produced through a common gathering point or shared facility of the common surface network. Thus, heterogeneous fluids from different reservoirs that flow into the common gathering point may combine or mix together. Thus, heterogeneous fluids from different reservoirs that flow into the common gathering point may combine or mix together. In an example, the disclosed embodiments may be used to calculate properties of the mixed fluids at the common gathering point or other points within the common surface network during a simulation of fluid production in the multi-reservoir system. One example of a reservoir simulator in which the disclosed embodiments may be implemented is the Nexus® integrated reservoir and surface simulator available from Landmark Graphics Corporation of Houston, Tex.

In an embodiment, the simulation may be based in part on production system data including various measurements collected downhole from a well drilled within each hydrocarbon reservoir, e.g., in the form of a production well for an oil and gas reservoir. Further, multiple production wells may be drilled for providing access to the reservoir fluids underground. Measured well data may be collected regularly from each production well to track changing conditions in the reservoir, as will be described in further detail below with respect to the production well examples illustrated in FIGS. 1A and 1B.

FIG. 1A is a diagram of an exemplary production well 100A with a borehole 102 that has been drilled into a reservoir formation. Borehole 102 may be drilled to any depth and in any direction within the formation. For example, borehole 102 may be drilled to ten thousand feet or more in depth and further, may be steered horizontally for any distance through the formation, as desired for a particular implementation. The production well 100A also includes a casing header 104 and a casing 106, both secured into place by cement 103. A blowout preventer (BOP) 108 couples to casing header 104 and a production wellhead 110, which together seal in the well head and enable fluids to be extracted from the well in a safe and controlled manner.

Measured well data may be periodically sampled and collected from the production well 100A and combined with measurements from other wells within a reservoir, enabling the overall state of the reservoir to be monitored and assessed. These measurements may be taken using a number of different downhole and surface instruments, including but not limited to, a temperature and pressure sensor 118 and a flow meter 120. Additional devices may also be coupled in-line to a production tubing 112 including, for example, a downhole choke 116 (e.g., for varying a level of fluid flow restriction), an electric submersible pump (ESP) 122 (e.g., for drawing in fluid flowing from perforations 125 outside ESP 122 and production tubing 112), an ESP motor 124 (e.g., for driving ESP 122), and a packer 114 (e.g., for isolating the production zone below the packer from the rest of well 100A). Additional surface measurement devices may be used to measure, for example, the tubing head pressure and the electrical power consumption of ESP motor 124.

FIG. 1B is a diagram showing an alternative embodiment of the production well 100A of FIG. 1A, which includes many of the same components as well 100A but has been adapted for artificial gas lift. As shown in FIG. 1B, a production well 100B further includes a gas lift injector mandrel 126 in addition to the above-described components of well 100A. In an embodiment, gas lift injector mandrel 126 is coupled in-line with production tubing 112 for controlling a flow of injected gas into a portion of production tubing 112 located above-ground or at the surface of the well near wellhead 110. Although not shown in FIG. 1B, the gas lift production well 100B may also include the same type of downhole and surface instruments as shown for production well 100A in FIG. 1A for providing the above-described measurements.

As shown in FIGS. 1A and 1B, each of the devices along production tubing 112 couples to a cable 128, which may be attached to an exterior portion of production tubing 112. Cable 128 may be used primarily to provide power to the devices to which it couples. Cable 128 also may be used to provide signal paths (e.g., electrical or optical paths), through which control signals may be directed from the surface to the downhole devices as well as telemetry signals from the downhole devices to the surface. The respective control and telemetry signals may be sent and received by a control unit 132 at the surface of the production well. Control unit 132 may be coupled to cable 128 through blowout preventer 108. In an embodiment, field personnel may use control unit 132 to control and monitor the downhole devices locally, e.g., via a user interface provided at a terminal or control panel integrated with control unit 132. Additionally or alternatively, the downhole devices may be controlled and monitored by a remote processing system 140. Processing system 140 may be used to provide various supervisory control and data acquisition (SCADA) functionality for the production wells associated with each reservoir in a field. For example, a remote operator may use processing system 140 to send appropriate commands for controlling wellsite operations to control unit 132. Communication between control unit 132 and processing system 140 may be via one or more communication networks, e.g., in the form of a wireless network (e.g., a cellular network), a wired network (e.g., a cabled connection to the Internet) or a combination of wireless and wired networks.

As shown in FIGS. 1A and 1B, processing system 140 may include a computing device 142 (e.g., a server) and a data storage device 144 (e.g., a database). Although only one computing device and one data storage device are shown in FIGS. 1A and 1B, it should be appreciated that processing system 140 may include additional computing devices and data storage devices. Computing device 142 may be implemented using any type of computing device having at least one processor, a memory and a networking interface capable of sending and receiving data to and from control unit 132 via a communication network. In an embodiment, computing device 142 may be a type of server. Examples of such a server include, but are not limited to, a web server, an application server, a proxy server, and a network server. In some implementations, computing device 142 may represent a group of computing devices in a server farm.

In an embodiment, control unit 132 may periodically send wellsite production data via a communication network to processing system 140 for processing and storage. Such wellsite production data may include, for example, production system measurements from various downhole devices, as described above. In some implementations, such production data may be sent using a remote terminal unit (RTU) of control unit 132. In an embodiment, data storage device 144 may be used to store the production data received from control unit 132. In an example, data storage device 144 may be used to store historical production data including a record of actual and simulated production system measurements obtained or calculated over a period of time, e.g., multiple simulation time-steps, as will be described in further detail below.

While production wells 100A and 100B are described in the context of a single reservoir, it should be noted that the embodiments disclosed herein are not limited thereto and that the disclosed embodiments may be applied to fluid production from multiple reservoirs in a multi-reservoir production system with a common surface or gathering network, as will be described in further detail below with respect to FIG. 3. Thus, a plurality of surface control units similar to control unit 132 may be used to send production system data from the respective wellsites of different reservoirs in the production system to processing system 140. In addition to the above-described SCADA functionality, processing system 140 may be used to process the received data and simulate fluid production in the multi-reservoir system, as will be described in further detail below.

Figure 2:
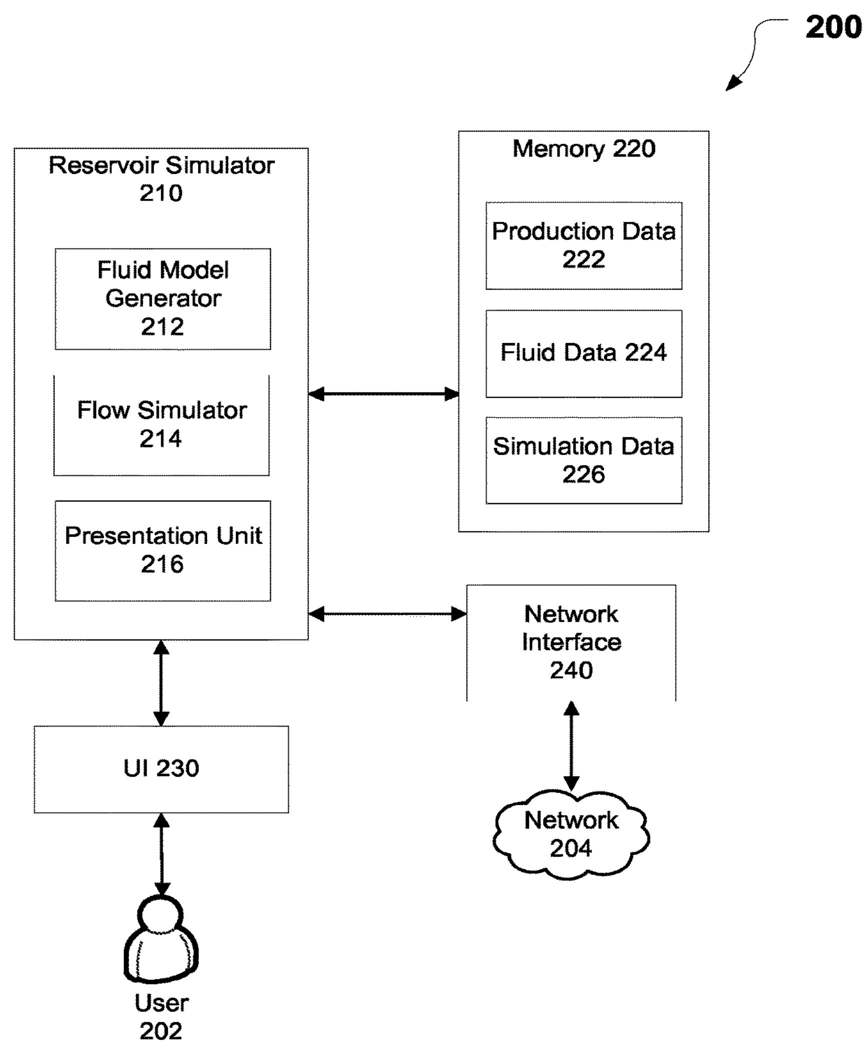
FIG. 2 is a block diagram of an exemplary system for simulating fluid production in a multi-reservoir system with a common surface network.

FIG. 2 is a block diagram of an exemplary system 200 for simulating fluid production in a multi-reservoir system. For example, system 200 may be used to implement a processing system, e.g., processing system 140 of FIGS. 1A and 1B, as described above, for processing wellsite data sent by a surface control unit (e.g., control unit 132 of FIGS. 1A and 1B) of a production well associated with each reservoir in the production system. As shown in FIG. 2, system 200 includes a reservoir simulator 210, a memory 220, a user interface (UI) 230 and a network interface 240. Reservoir simulator 210 includes a fluid model generator 212, a flow simulator 214 and a data presentation unit 216. In an embodiment, reservoir simulator 210 and its components (including fluid model generator 212, flow simulator 214 and presentation unit 216), memory 220, UI 230 and network interface 240 may be communicatively coupled to one another via an internal bus of system 200.

In an embodiment, system 200 can be implemented using any type of computing device having at least one processor and a processor-readable storage medium for storing data and instructions executable by the processor. Examples of such a computing device include, but are not limited to, a desktop computer, a workstation, a server, a cluster of computers (e.g., in a server farm) or similar type of computing device. Such a computing device may also include an input/output (I/O) interface for receiving user input or commands via a user input device (not shown). The user input device may be, for example and without limitation, a mouse, a QWERTY or T9 keyboard, a touch-screen, a graphics tablet, or a microphone. The I/O interface may also include a display interface for outputting or presenting information on a display (not shown) coupled to or integrated with the computing device.

While only reservoir simulator 210, memory 220, UI 230 and network interface 240 are shown in FIG. 2, it should be appreciated that system 200 may include additional components, modules, and/or sub-components as desired for a particular implementation. It should also be appreciated that reservoir simulator 210 and its components may be implemented in software, firmware, hardware, or any combination thereof. Furthermore, it should be appreciated that embodiments of reservoir simulator 210, or portions thereof, can be implemented to run on any type of processing device including, but not limited to, a computer, workstation, embedded system, networked device, mobile device, or other type of processor or computer system capable of carrying out the functionality described herein.

In an embodiment, system 200 may use network interface 240 to communicate with different devices and other systems via a network 204. Network 204 can be any type of network or combination of networks used to communicate information between different computing devices. Network 204 can include, but is not limited to, a wired (e.g., Ethernet) or a wireless (e.g., Wi-Fi or mobile telecommunications) network. In addition, network 204 can include, but is not limited to, a local area network, medium area network, and/or wide area network such as the Internet.

In an embodiment, system 200 may use network interface 240 to send and receive information to and from a wellsite control and monitoring device, e.g., surface control unit 132 of FIGS. 1A and 1B, as described above, via network 204. Such information may include, for example, production system data sent from the wellsite control and monitoring device to system 200 via network 204. Likewise, various control signals and commands may be sent by system 200 to the wellsite control and monitoring device via network 204, e.g., for purposes of controlling wellsite operations or requesting wellsite production system data from the device. In some implementations, such control signals may be in the form of telemetry signals sent using a telemetry transceiver integrated within network information 240 of system 200.

In an embodiment, the control signals or commands sent by system 200 to the device at the wellsite may be based on input received from a user 202 via UI 230. User 202 may interact with UI 230 via a user input device (e.g., a mouse, keyboard, or touch-screen) and a display coupled to system 200 to configure, control or monitor the execution of production system simulation. In accordance with user input received by reservoir simulator 210 via UI 230, production system data may be requested and received from a wellsite control and monitoring device via network 204, as described above. The data received from the device may be processed and used by reservoir simulator 210 in the production system simulation. The results of the simulation may then be presented by presentation unit 216 to user 202 via UI 230.

In an embodiment, memory 220 may be used to store the production system data from the device in the above example in addition to various other types of data accessible by reservoir simulator 210 and its components (including fluid model generator 212, flow simulator 214 and presentation unit 216) for implementing the production system simulation functionality disclosed herein. Memory 220 can be any type of recording medium coupled to an integrated circuit that controls access to the recording medium. The recording medium can be, for example and without limitation, a semiconductor memory, a hard disk, or similar type of memory or storage device. In some implementations, memory 220 may be a remote cloud-based storage location accessible to system 200 via network interface 240 and network 204.

In the example shown in FIG. 2, the data stored in memory 220 may include production data 222, fluid data 224 and simulation data 226. As will be described in further detail below, reservoir simulator 210 may use a combination of production data 222, fluid data 224 and simulation data 226 to derive a desired set of operating points for a given time-step of the production system simulation.

Production data 222 may include, for example, actual and/or simulated production system measurements. Actual production system measurements may include, for example, surface and downhole well measurements from various production wells in the multi-reservoir system. Such measurements may include, but are not limited to, pressure, volume, temperature and fluid flow measurements taken downhole near the well perforations, along the production string, at the wellhead and within the gathering network prior to the point where the fluids mix with fluids from other reservoirs. Likewise, the simulated measurements may include, for example and without limitation, estimates of pressure, temperature and fluid flow. Such estimates may be determined based on, for example, simulation results from one or more previous time-steps.

Fluid data 224 may represent different reservoir fluid components (e.g., heavy crude, light crude, methane, etc.) and related properties including, for example, their proportions, fluid density and viscosity for various compositions, pressures and temperatures, or other data.

In an embodiment, fluid model generator 212 may generate a fluid model for each reservoir in the multi-reservoir system based on corresponding production data 222 and fluid data 224. For example, fluid model generator 212 may determine parameters for each fluid component or group of components of the reservoir based on actual and simulated production system measurements (e.g., from one or more prior simulation time-steps) and fluid component characterizations associated with each reservoir. The resulting model for each component/group can then be applied to known state variables to calculate unknown state variables at each simulation point or "gridblock" within the reservoir, at the wellbore perforations or "sandface," and within the common gathering network of the production system. These unknown variables may include, for example and without limitation, each gridblock's liquid volume fraction, solution gas-oil ratio and formation volume factor.

In an embodiment, the resulting fluid component state variables, both measured and calculated, may be provided as inputs to flow simulator 214 for simulating the flow of fluids through the multi-reservoir production system. Additional inputs to flow simulator 214 may include, for example, various floating parameters, fixed parameters and characterization data related to the production system and constraints thereof. The floating parameters may include, for example, various enhanced oil recovery (EOR) parameters including, but not limited to, gas lift injection rates, reservoir gas injection rates and reservoir liquid injection rates. Examples of fixed parameters may include facility constraints (e.g., a production capacity limit) and default production rates for individual wells. Reservoir characterization data may include, for example, geological data describing reservoir formations (e.g., log data previously collected during drilling and/or prior logging of the well) and formation characteristics (e.g., porosity). The above-described fluid component state variables along with the other simulation inputs, parameters and production system constraints may be stored in memory 220 as simulation data 226.

In an embodiment, flow simulator 214 may employ set of a fully-coupled equations to perform the simulation and determine optimal operating settings for the production system such that production of the reservoirs can be maximized over time without exceeding any facility constraints. The equations are characterized as "fully-coupled" because all the equations for all the reservoirs and the gathering network may be solved simultaneously, rather than solving the reservoir and gathering network separately and iterating between the reservoir and gathering network solutions to determine appropriate boundary conditions for each set of equations (i.e., loosely-coupled).

In an embodiment, the fully-coupled equations may be used with any of various numerical analysis techniques (e.g., a Newton-Raphson method) to determine a set of mass and/or volume balance values for each gridblock. The equations also may be used to determine the flow of fluids through the production system and provide a solution that includes operating settings that honor the various production system constraints, e.g., one or more facility constraints, gathering network constraints, well constraints, or reservoir constraints. Further, the equations may be used by flow simulator 214 to determine updated fluid properties (e.g., updated fluid component mass and volume values for each gridblock) at the end of the simulation time-step. At least some of the updated parameters may be provided, for example, as previous time-step data for subsequent simulation time-steps. In addition, the simulation performed by flow simulator 214 may be repeated for each of a plurality of different time-steps, where the simulation results for a given time-step are used to update the simulation for the next time-step.

With the state of the fluids known throughout the production system, the flow of fluid can be simulated using mass/volume balance equations representative of the reservoir, of perforations in the wellbore and of the gathering network. In an embodiment, the facility equations representing the gathering network include molar balance equations at the nodes, hydraulic equations, constraint equations, and composition equations. The independent variables for the facility equations include pressure and composition for the nodes, and molar flow rates for the connections.

The full system of equations can be expressed as follows:

$$\begin{bmatrix} A_{rr} & & A_{rf} \\ & A_{pp} & A_{pf} \\ & A_{fp} & A_{ff} \end{bmatrix} \begin{bmatrix} \delta x_r \\ \delta x_p \\ \delta x_f \end{bmatrix} = -\begin{bmatrix} R_r \\ R_p \\ R_f \end{bmatrix} \tag{1}$$

where R denotes the residuals, and A the Jacobian for a Newton iteration of the production system simulation. A contains the derivatives of the residuals with respect to the variables x, where $x_r$ includes gridblock moles and pressures, $x_p$ includes perforation flow rates, and $x_f$ includes facility node compositions and pressures and the total molar flow rate to of the facility connections. The first row of equations represents the reservoir equations (simulating fluid flow through the reservoir), the second row represents the perforation equations (simulating fluid flow through the perforations), and the third row represents the facility equations (simulating fluid flow through the gathering network).

In an embodiment, the reservoir equations include molar balance equations of the form:

$$R_{ri}=F_i^{in}-F_i^{out}-a_i+G_i-\Sigma_{pep_s}Q_{rpi} \tag{2}$$

where the residual $R_{ri}$ of component i for each reservoir gridblock r is driven to zero at full convergence of the equations. For component i, $F_i^{in}$ and $F_i^{out}$ are the molar flow rates across reservoir gridblock faces, $a_i$ is the rate of accumulation, $G_i$ is the rate of generation and $Q_{rpi}$ is the perforation flow rate (positive for production, negative for injection) between a reservoir gridblock r and a wellbore through perforation p. The $Q_{rpi}$ are summed over the perforations within gridblock r. The independent variables are the mass (in moles) of each component i, and the gridblock pressure. In addition to the molar balance equations, in at least some illustrative embodiments a volume balance equation operates to constrain the pore volume so that it equals the fluid volume. This can be written in residual form as:

$$R_{r,nc_r+1}=V_{Pr}-V_{Fr} \tag{3}$$

where $nC_r$ is the number of reservoir pseudo-components, $V_{Pr}$ is the pore volume and $V_{Fr}$ is the fluid volume for gridblock r.

In at least some illustrative embodiments, the perforation equations are expressed as flow equations for each perforation within a reservoir gridblock. Starting with the simpler case of a single reservoir and a gathering network with the same number of pseudo-components, the perforation equation for producing perforations can be expressed using the flow equation, $$Q_{rpi} = C_p\Delta\Phi_p \sum_{m=1}^{N_{phases}} \frac{krel_{rm}}{\mu_{rm}}\rho_{rm}z_{rmi} \tag{4}$$

where $Q_{rpi}$ is the perforation flow rate of fluid pseudo-component i for perforation p within gridblock r, $C_p$ is the wellbore constant (equal to the well index multiplied by the permeability-thickness product), $\Delta\Phi_p$ is the permeability-thickness product (i.e., the potential difference from the reservoir to the wellbore for perforation p), and where for phase m within gridblock r, $krel_{rm}$ is the relative permeability, $\mu_{rm}$ is the viscosity, $\rho_{rm}$ is the density, and $z_{rmi}$ is the mole fraction of fluid pseudo-component i. Similarly, the perforation equation for injecting perforations can be expressed using the flow equation, $$Q_{rpi}=C_p\lambda_p^{inj}\rho_p^{inj}\Delta\Phi_p z_{rpi} \tag{5}$$

where $\lambda_p^{inj}$ is the fluid mobility (e.g., the sum of the gridblock phase mobilities or an endpoint mobility), $\rho_p^{inj}$ is the perforation-injected fluid density, and $z_{rpi}$ is the component mole fraction at a node in the wellbore.

The above-described simulation assumes a configuration of the production system in which multiple reservoirs are coupled to a common surface or gathering network. Such a gathering network may include, for example, a plurality of nodes with connections between the nodes and various reservoir gridblocks. Nodes may represent physical locations of relevant components or devices (e.g., separator 310 of FIG. 3, as will be described below) within the gathering network and/or the production wells of various reservoirs. Connections may represent pipes or flow control devices, for example, pumps, compressors, valves, or similar types of devices. An example of such a production system configuration is shown in FIG. 3.

The above-described simulation assumes a configuration of the production system in which multiple reservoirs are coupled to a common surface or gathering network. Such a gathering network may include, for example, a plurality of nodes with connections between the nodes and various reservoir gridblocks. Nodes may represent physical locations of relevant components or devices within the gathering network and/or the production wells of various reservoirs. Connections may represent pipes or flow control devices, for example, pumps, compressors, valves, or similar types of devices. An example of such a production system configuration is shown in FIG. 3.

Figure 3:
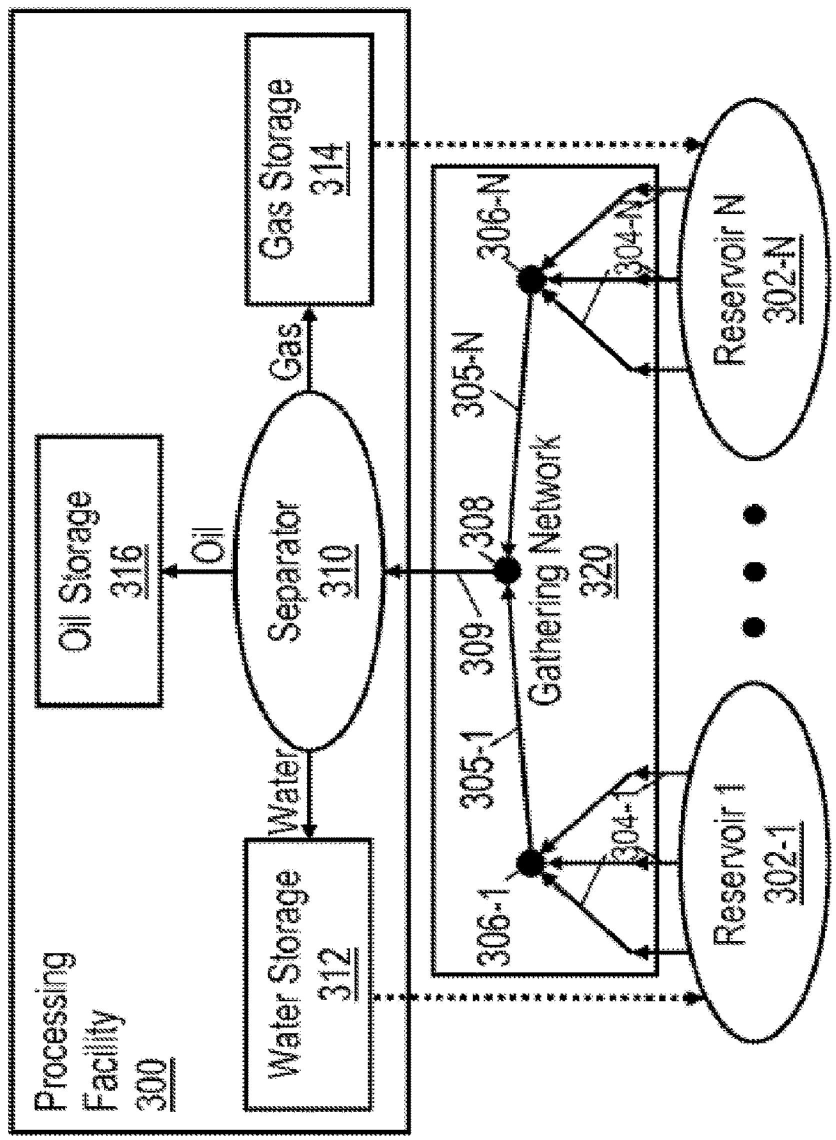
FIG. 3 is a diagram illustrating an exemplary of a multi-reservoir system with a common surface network.

FIG. 3 is a diagram illustrating an exemplary multi-reservoir system including a common surface or gathering network. As shown in FIG. 3, a group of N reservoirs 302-1 through 302-N are coupled together through a gathering network 320. Individual well lines 304 (1 through N) from each well couple to a corresponding reservoir node 306 (1 through N), with each node coupling through a reservoir line 305 (1 through N) to a common node 308. Common node 308 may provide, for example, mixed fluids produced from reservoirs 302-1 to 302-N through riser 309 to a processing facility 300. The mixed fluids that are produced at common node 308 through riser 309 may include fluids produced from any number of reservoirs 302-1 to 302-N, for example, all of the reservoirs or any subset thereof. In the example shown, processing facility 300 includes a separator 310 that is receives the mixed product from facility riser 309 and separates the product into water, oil and gas. These separated products are respectively stored in water storage 312, oil storage 316 and gas storage 314 for later use and/or delivery further downstream (e.g., to a refining facility). Alternatively, some of the separated product may be used to assist with the removal of product from the reservoir. For example, a portion of the separated gas and/or water may be reinjected into one or more reservoirs as part of an enhanced oil recovery (EOR) operation, as indicated by the dashed arrows in FIG. 3.

Maximizing fluid production in the multi-reservoir production system of FIG. 3 may involve controlling the production of each individual well such that the combined production of the wells, or a selected group of the wells, provides the greatest possible amount of hydrocarbon (e.g., oil and/or gas) production within the operating limits of processing facility 300 and without exceeding any production system constraints. In an embodiment, optimal well operating points that maximize fluid production over time and enable processing facility 300 to operate within its limits may be determined from the results of a simulation of fluid production in the multi-reservoir system. For example, reservoir simulator 210 of FIG. 2, as described above, may be used to identify the optimal well operating points from a simulation of fluid production in the multi-reservoir system of FIG. 3 based on production system measurements, reservoir characterizations and constraints related to reservoirs 302-1 to 302-N and processing facility 300. In some implementations, such operating points may be expressed as a solution to a simultaneous set of fully-coupled equations, as described above.

In addition to using simulation results to determine optimal well operating points and maximize fluid production in the multi-reservoir system, a reservoir engineer (e.g., user 202 of reservoir simulator 210 of FIG. 2) might be interested in improving the computational efficiency of the simulation itself and the accuracy of the simulation results. As will be described in further detail below, the fluid modeling and production simulation techniques disclosed herein may allow such improvements to be achieved for the to simulation by using a shared or common EOS characterization representing mixed fluids produced from different reservoirs of the above-described multi-reservoir production system. Accordingly, advantages of such a common characterization include facilitating the calculation of mixed fluid properties at points in the common surface network where the source of fluids may be from different petroleum reservoirs coupled to the network.

Figure 4:
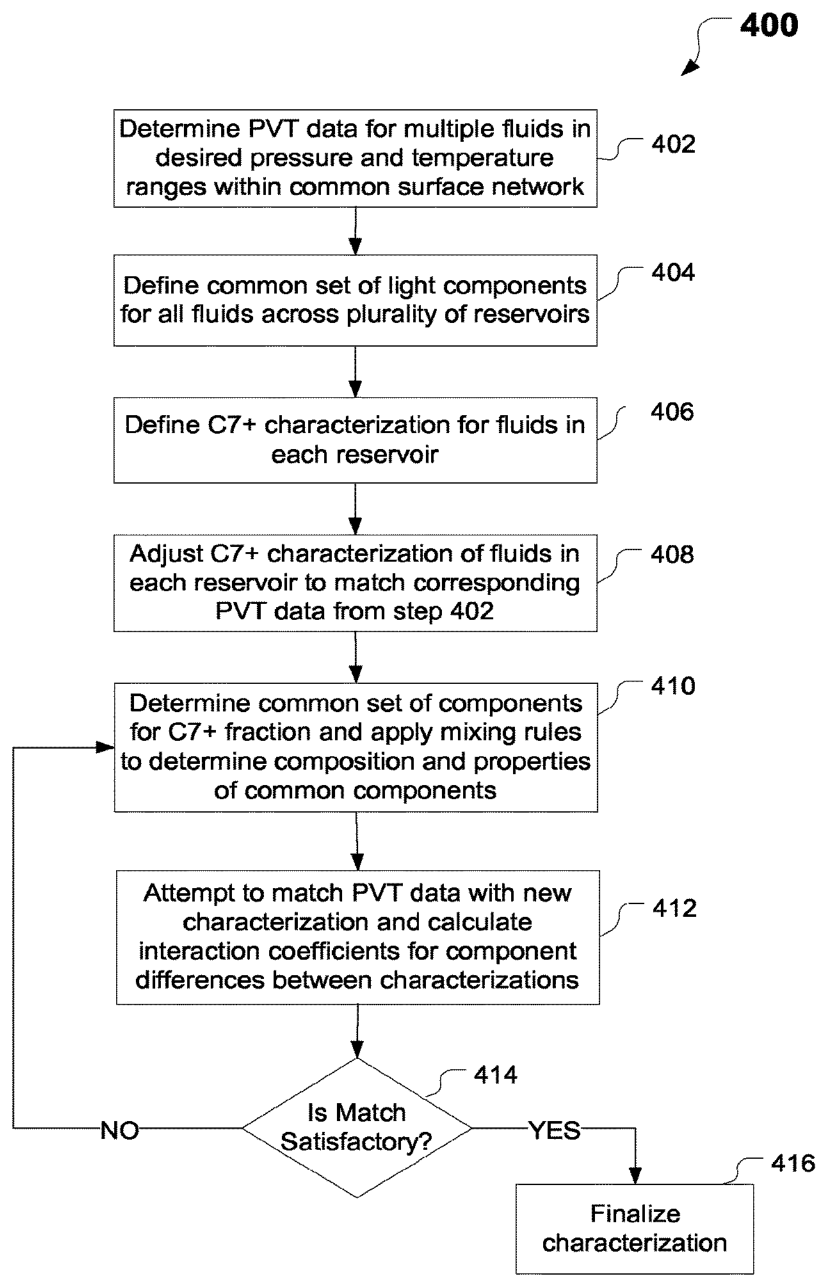
FIG. 4 is a flowchart of an exemplary method of generating a shared equation of state (EOS) characterization of multiple fluids in a multi-reservoir system with a common surface network.

FIG. 4 is a flowchart of an exemplary method 400 of using a shared EOS characterization of multiple fluids to simulate fluid production in a multi-reservoir system with a common surface network. For discussion purposes, method 400 will be described using the above-described multi-reservoir system of FIG. 3 but is not intended to be limited thereto. As shown in FIG. 4, method 400 includes steps 402, 404, 406, 408, 410, 412, 414 and 416. However, it should be noted that method 400 may include additional steps to perform the techniques disclosed herein, as desired for a particular implementation. The steps of method 400 may be implemented using, for example, reservoir simulator 210 of FIG. 2, as described above, but method 400 is not intended to be limited thereto.

Method 400 may be used, for example, to characterize multiple fluids or fluid sets across a plurality of reservoirs (e.g., reservoirs 302-1 to 302-N of FIG. 3) within the multi-reservoir system. In one embodiment, an EOS characterization of the multiple fluids may be generated based on raw laboratory data related to the behavior of the fluids at different points in the common surface network. However, such data may be unavailable, particularly for the ranges of compositions, temperatures and pressures of interest in the parts of the surface network where fluids from different reservoir sources commingle. In many cases, the only information that may be available is the EOS characterization that has already been established for each reservoir fluid by different operators or scientists. However, the previously established EOS characterizations may have a vastly different number of components and component properties. Regardless of such differences, they still may be used to generate synthetic laboratory data sets, which in turn can be used to create a new EOS characterization for the fluids, as will be described in further detail below with respect to the steps of method 400. In an embodiment, the new EOS characterization will apply only to multiple fluids produced at shared points in the network from different reservoirs in the multi-reservoir system. For other points in the common surface network where fluids are produced from only a single reservoir, the original or previously established EOS characterization associated with the fluids of the particular reservoir may be used instead.

Method 400 begins in step 402, which includes determining pressure-volume-temperature (PVT) data for multiple fluids in the common surface network. In an embodiment, the PVT data in step 402 may be based on existing raw laboratory data determined to match the fluid behavior at points in the common surface network where is fluids produced from different reservoirs may mix or commingle together. For example, step 402 may include selecting existing PVT data in a desired range of temperature and pressure conditions used in common or shared points at which mixed fluids are produced in the common surface network. Alternatively, in cases where such data may not be available, step 402 may include generating artificial or synthetic PVT data in the desired range of pressure and temperature conditions based on previously established EOS characterizations for the reservoir fluids, as described above.

Method 400 then proceeds to step 404, which includes defining a common characterization with a common set of light components for each reservoir fluid or fluid set in this example. In an embodiment, the common set of light components may be defined. Examples of the light components in such a common set include, but are not limited to, the following compounds: carbon dioxide (CO2); hydrogen sulfide (H2S); nitrogen (N2); methane (C1); ethane (C2), propane (C3); normal butane (nC4); iso-butane (iC4); normal pentane (nC5); iso-pentane (iC5); and normal hexane (C6). In an embodiment, the set of light components defined for all reservoir fluids may also have the same EOS properties, except for interaction coefficients with respect to heavy components. Thus, the above-listed compounds may have, for example, the same properties (e.g., identical EOS properties) across all fluid characterizations. In some implementations, the EOS properties may be set by a user (e.g., user 202 of reservoir simulator 210 of FIG. 2, as described above).

In step 406, different characterizations may be defined for fractions of the C7+ heavy components of each reservoir fluid or fluid set. In an embodiment, the C7+ heavy components may be defined using a probability distribution function that provides the molecular weight and mole fraction for each carbon number from C7 to some predefined upper bound, e.g., ranging from C45 to C200. It should be appreciated that any of various techniques may be used to characterize the C7+ fractions. In an embodiment, the characterization for the C7+ fractions of each fluid may be defined with the constraint that the overall molecular weight matches the specific gravity of the C7+ fraction of each fluid. However, the molecular weight may be varied, for example, by a certain percentage (e.g., 20%), for purposes of matching the saturation pressure of a particular fluid. In step 408, the C7+ characterization defined in step 406 may be adjusted to match the PVT data for each individual fluid set, i.e., without regard for common fluid components.

In step 410, a common set of components may be determined for the C7+ range of fluid components. In an embodiment, the common components may be determined based on user input, for example, as received via UI 230 of reservoir simulator 210 of FIG. 2, as described above. For example, the user may specify a set of components to be matched in the C7+ range. It may be required that for the components to be common, they must have the same fluid properties (exclusive of interaction coefficients) over multiple characterizations. In an embodiment, the common components may be determined by converting the specified components into a common data set using any of various well-known techniques. Such a technique may include, for example and without limitation: determining a set of common components that are grouped by molecular weight range; for each fluid, calculating the properties of the common components by lumping together the properties of individual components, where properties of components may be weighted by the mole fraction of that component; and for each common component between fluids, calculating the average property for each component by using a weighted factor assigned to each fluid. The same weighting factor may be used for each property. Examples of properties that may be calculated include, but are not limited to, the mole fraction, the molecular weight, the critical temperature, the critical pressure, and the acentric factor.

However, in contrast with conventional characterization techniques, the disclosed embodiments may use a different set of components representing the components in the C7+ range. In an embodiment, each fluid may include at least one unique heavy component that is different from other reservoir fluids.

In one embodiment, the a component mixing or grouping process derives new interaction coefficients for new hydrocarbon pairs using a Cheuh-Prausnitz technique, which may be expressed by the following equation:

$$k_{ij=A}\left[1-\left(\frac{2v_i^{2/6}v_j^{2/6}}{v_{ci}^{\varepsilon/5}+v_{cj}^{\varepsilon/5}}\right)^B\right],$$

where $k_{ij}$ is the interaction coefficient between components i and j, A is an to empirical constant (e.g., 0.18), and $v_{ci}$ is the critical molar volume of component i.

Method 400 may then proceed to step 412, which includes attempting to re-match the data with the new fluid characterization. In one embodiment, step 412 may include determining whether the sum of the differences between the measured data and the calculated data exceeds a predetermined tolerance range or threshold. As an example, the process might measure density at a particular pressure and temperature and compare it to the calculated value. This difference gets added to the errors of other measured and calculated differences. In one embodiment, the errors may be weighted based on the importance of the property. The process will compare the summed difference to a tolerance range to determine whether the match is satisfactory. In step 414, if it is determined that the match is satisfactory, method 400 repeats step 410 for additional C7+ fractions in the range of interest. If the match is not satisfactory, method 400 proceeds to step 416, in which the characterization is finalized, e.g., for use during simulation.

Accordingly, the disclosed embodiments provide a novel and efficient procedure for shared equation of state characterization of multiple fluids that would enable the prediction of combined fluids in a common surface network. One difference between the disclosed embodiments and prior methods is that prior methods require a conversion as soon as a fluid enters into a common area, regardless of whether the fluids are mixed or not, i.e., try to match all the PVT data in both the reservoir and the surface, whereas the disclosed embodiments will let the original description of the fluids persist until they get to point where there is actual mixing. In other words, the disclosed embodiments are limited to matching only the data in the common surface network and will let the original characterizations calculate phase behavior in the individual reservoirs and in the sections of the surface network that have no fluid commingling. This significantly improves the chances of success.

Another unique aspect of the disclosed embodiments over previous mechanisms is that prior mechanisms require that each of the fluids have the same number of components (i.e., every fluid must be converted to the same number of components), whereas the disclosed embodiments will have some common components and possibly one or more unique components for each reservoir. This unique marker component(s) will enable the process to forecast mixing. This characterization is intended for use in a flexible numerical reservoir simulator, such as, but not limited to, Nexus® reservoir simulator available from Landmark Graphics Corporation of Houston, Tex., in which the component sets can differ for different reservoirs, and within the surface network.

The disclosed embodiments may be implemented within, for example, an integrated reservoir and surface network simulator, as described above. The disclosed embodiments may be used, for example, as a basis for calculating the fluid properties of fluids that are created from the mixing of fluids from different reservoirs in different proportions. Accordingly, the disclosed embodiments may allow operators to keep their original fluid characterizations, while creating a reasonable basis for mixing fluids with vastly different characterizations.

Figure 5:
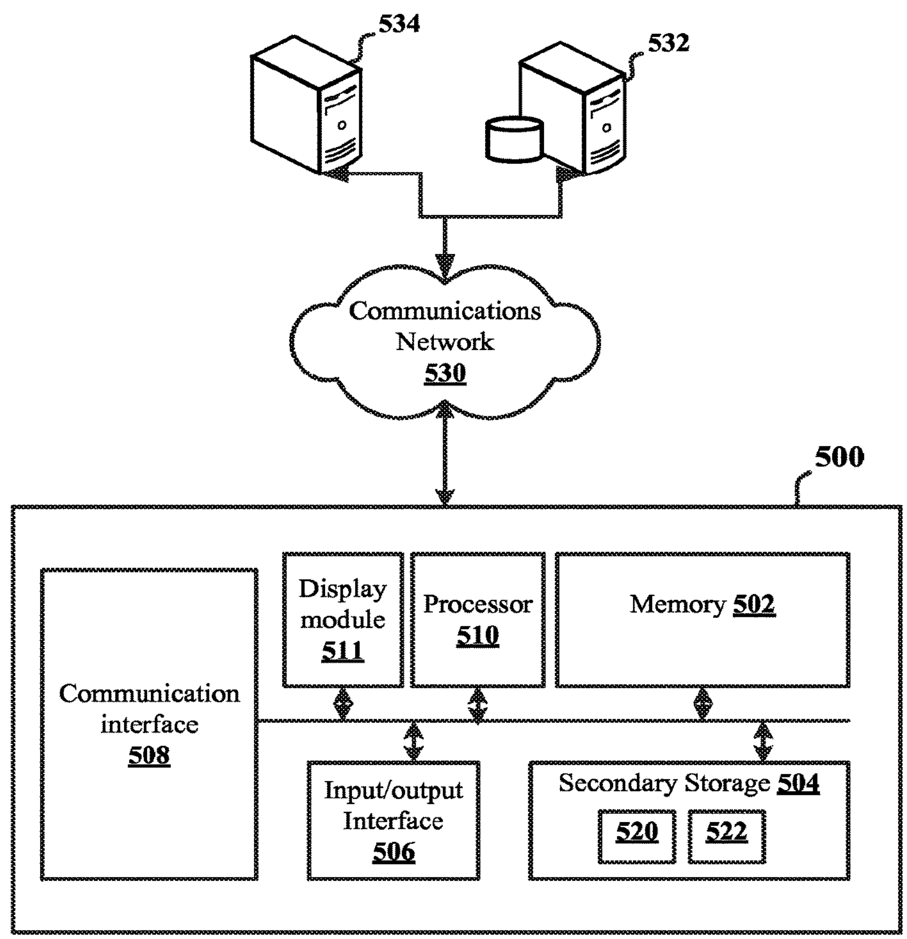
FIG. 5 is a block diagram of an exemplary computer system in which embodiments of the present disclosure may be implemented.

FIG. 5 is a block diagram of an exemplary computer system 500 in which embodiments of the present disclosure may be implemented. The system 500 may be any type of computing device including, but not limited to, a desktop computer, a laptop, a server, a tablet, and a mobile device. The system 500 includes, among other components, a processor 510, main memory 502, secondary storage unit 504, an input/output interface module 506, and a communication interface module 508.

The processor 510 may be any type or any number of single core or multi-core processors capable of executing instructions for performing the features and functions of the disclosed embodiments. The input/output interface module 506 enables the system 500 to receive user input (e.g., from a keyboard and mouse) and output information to one or more devices such as, but not limited to, printers, external data storage devices, and audio speakers. The system 500 may optionally include a separate display module 511 to enable information to be displayed on an integrated or external display device. For instance, the display module 511 may include instructions or hardware (e.g., a graphics card or chip) for providing enhanced graphics, touchscreen, and/or multi-touch functionalities associated with one or more display devices.

Main memory 502 is volatile memory that stores currently executing instructions/data or instructions/data that are prefetched for execution. The secondary storage unit 504 is non-volatile memory for storing persistent data. The secondary storage unit 504 may be or include any type of data storage component such as a hard drive, a flash drive, or a memory card. In one embodiment, the secondary storage unit 504 stores the computer executable code/instructions and other relevant data for enabling a user to perform the features and functions of the disclosed embodiments.

For example, in accordance with the disclosed embodiments, the secondary storage unit 504 may permanently store executable code/instructions 520 for performing the above-described procedure for using a modified black oil model for calculating mixing of different fluids in a common surface network. The executable code/instructions 520 are then loaded from the secondary storage unit 504 to main memory 502 during execution by the processor 510 for performing the disclosed embodiments. In addition, the secondary storage unit 504 may store other executable code/instructions and data 522 such as, but not limited to, a reservoir simulation application (e.g., Nexus® reservoir simulation software) for use with the disclosed embodiments.

The communication interface module 508 enables the system 500 to communicate with the communications network 530. For example, the network interface module 508 may include a network interface card and/or a wireless transceiver for enabling the system 500 to send and receive data through the communications network 530 and/or directly with other devices.

The communications network 530 may be any type of network including a combination of one or more of the following networks: a wide area network, a local area network, one or more private networks, the Internet, a telephone network such as the public switched telephone network (PSTN), one or more cellular networks, and/or wireless data networks. The communications network 530 may include a plurality of network nodes (not depicted) such as routers, network access points/gateways, switches, DNS servers, proxy servers, and other network nodes for assisting in routing of data/communications between devices.

For example, in one embodiment, the system 500 may interact with one or more servers 534 or databases 532 for performing the features of the disclosed embodiments. For instance, the system 500 may query the database 532 for well log information for creating a reservoir model in accordance with the disclosed embodiments. Further, in certain embodiments, the system 500 may act as a server system for one or more client devices or a peer system for peer to peer communications or parallel processing with one or more devices/computing systems (e.g., clusters, grids).

As described above, embodiments of the present disclosure, including the modified black oil modeling techniques disclosed herein, are particularly useful for calculating properties of mixed fluids produced in a multi-reservoir system with a common surface network. In one embodiment of the present disclosure, a computer-implemented method of fluid production in a multi-reservoir system with a common surface network includes: determining pressure-volume-temperature (PVT) data for fluids in each of a plurality of reservoirs coupled to the common surface network; generating a shared equation of state (EOS) characterization representing each of the fluids across the plurality of reservoirs, based on the corresponding PVT data for the fluids in each reservoir; calculating data representing properties of the fluids in each reservoir, based on the shared EOS characterization of the fluids; determining whether or not the calculated data matches the PVT data associated with the fluids in each reservoir; and when the calculated data is determined not to match the PVT data, adjusting the shared EOS characterization based on a difference between the calculated data and the PVT data.

In a further embodiment, the PVT data is based on existing data within a range of temperature and pressure conditions within the common surface network. In yet a further embodiment, the PVT data is generated based on a previously established EOS characterization associated with the fluids in each reservoir. In yet a further embodiment, the method includes defining a common set of light components with identical EOS properties for use by all fluid characterizations. In yet a further embodiment, the method includes defining a C7+ characterization for the fluids in each of the plurality of reservoirs. In yet a further embodiment, the method includes adjusting a molecular weight of a C7+ fraction to match a saturation pressure thereof. In yet a further embodiment, the method includes individually matching each PVT data for each fluid set by adjusting the C7+ characterization of each fluid, without regard for common components. In yet a further embodiment, the method includes determining a common component set for the C7+ fraction and applying mixing rules to determine composition and properties of common components.

In another embodiment of the present disclosure, a system for defining non-linear petrofacics for a reservoir simulation model includes at least one processor and a memory coupled to the processor has instructions stored therein, which when executed by the processor, cause the processor to perform functions, including functions to: determine pressure-volume-temperature (PVT) data for fluids in each of a plurality of reservoirs coupled to the common surface network; generate a shared equation of state (EOS) characterization representing each of the fluids across the plurality of reservoirs, based on the corresponding PVT data for the fluids in each reservoir; calculate data representing properties of the fluids in each reservoir, based on the shared EOS characterization of the fluids; determine whether or not the calculated data matches the PVT data associated with the fluids in each reservoir; and when the calculated data is determined not to match the PVT data, adjust the shared EOS characterization based on a difference between the calculated data and the PVT data.

In yet another embodiment of the present disclosure, a computer-readable storage medium has instructions stored therein, which when executed by a computer cause the computer to perform a plurality of functions, including functions to: determine pressure-volume-temperature (PVT) data for fluids in each of a plurality of reservoirs coupled to the common surface network; generate a shared equation of state (EOS) characterization representing each of the fluids across the plurality of reservoirs, based on the corresponding PVT data for the fluids in each reservoir; calculate data representing properties of the fluids in each reservoir, based on the shared EOS characterization of the fluids; determine whether or not the calculated data matches the PVT data associated with the fluids in each reservoir; and when the calculated data is determined not to match the PVT data, adjust the shared EOS characterization based on a difference between the calculated data and the PVT data.

While specific details about the above embodiments have been described, the above hardware and software descriptions are intended merely as example embodiments and are not intended to limit the structure or implementation of the disclosed embodiments. For instance, although many other internal components of the system 500 are not shown, those of ordinary skill in the art will appreciate that such components and their interconnection are well known.

In addition, certain aspects of the disclosed embodiments, as outlined above, may be embodied in software that is executed using one or more processing units/components. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives, optical or magnetic disks, and the like, which may provide storage at any time for the software programming.

Additionally, the flowchart and block diagrams in the figures illustrate the architecture, functionality, and operation of possible implementations of systems, methods and computer program products according to various embodiments of the present invention. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The above specific example embodiments are not intended to limit the scope of the claims. The example embodiments may be modified by including, excluding, or combining one or more features or functions described in the disclosure.

What is claimed is:

1. A computer-implemented method of controlling fluid production in a multi-reservoir system with a common surface network, the method comprising:

determining, by a computer system, pressure-volume-temperature (PVT) data for fluids in each of a plurality of reservoirs coupled to the common surface network, based on an initial equation of state (EOS) characterization of the fluids in each reservoir, the initial EOS characterization for each reservoir including a set of light fluid components that are common across the plurality of reservoirs and at least one heavy fluid component that is unique to that reservoir;

generating, by the computer system, a shared EOS characterization representing each of the fluids across the plurality of reservoirs, based on the corresponding PVT data for the fluids in each reservoir;

simulating fluid production in the multi-reservoir system for a gathering point in the common surface network, based on the shared EOS characterization and the initial EOS characterization for each of the plurality of reservoirs;

determining whether or not the simulated fluid production for the gathering point includes mixed fluids from different reservoirs in the plurality of reservoirs;

when the simulated fluid production for the gathering point is determined not to include mixed fluids from different reservoirs, calculating first data representing properties of fluids to be produced at the gathering point using the initial EOS characterization for a corresponding one of the plurality of reservoirs;

when the simulated fluid production for the gathering point is determined to include mixed fluids from different reservoirs:

calculating second data representing properties of the mixed fluids to be produced at the gathering point using the shared EOS characterization of the plurality of reservoirs;

determining whether or not the second data matches the PVT data associated with each reservoir from which the mixed fluids are to be produced at the gathering point;

when the second data is determined not to match the PVT data, adjusting the shared EOS characterization based on a difference between the second data and the PVT data; and repeating the calculating of the second data, the determining, and the adjusting until the second data is determined to match the PVT data associated with the mixed fluids;

determining, by the computer system, operating settings for a production well associated with each reservoir from which fluids are to be produced at the gathering point in the common surface network, based on at least one of the first data or the second data; and controlling, by the computer system using control signals transmitted via a communication network to a wellsite control unit for the production well, production operations at the production well according to the determined operating settings.

2. The method of claim 1, wherein the PVT data is based on existing data within a range of temperature and pressure conditions within the common surface network.

3. The method of claim 1, wherein the initial EOS characterization for each reservoir includes a previously established EOS characterization for the fluids in that reservoir, and the PVT data is generated based on the previously established EOS characterization.

4. The method of claim 1, wherein generating the shared EOS characterization further comprises defining a common set of light components with identical EOS properties for use by all fluid characterizations.

5. The method of claim 4, further comprising defining a C7+ characterization for the fluids in each of the plurality of reservoirs.

6. The method of claim 5, further comprising adjusting a molecular weight of a C7+ fraction to match a saturation pressure thereof.

7. The method of claim 6, further comprising individually matching the PVT data for the fluids in each reservoir by adjusting the C7+ characterization of each fluid, without regard for common components.

8. The method of claim 7, further comprising determining a common component set for the C7+ fraction and applying mixing rules to determine composition and properties of common components.

9. A system comprising:

at least one processor; and a memory coupled to the processor having instructions stored therein, which when executed by the processor, cause the processor to perform functions including functions to:

determine pressure-volume-temperature (PVT) data for fluids in each of a plurality of reservoirs coupled to a common surface network, based on an initial equation of state (EOS) characterization of the fluids in each reservoir, the initial EOS characterization for each reservoir including a set of light fluid components that are common across the plurality of reservoirs and at least one heavy fluid component that is unique to that reservoir;

generate a shared EOS characterization representing each of the fluids across the plurality of reservoirs, based on the corresponding PVT data for the fluids in each reservoir;

simulate fluid production from the plurality of reservoirs to a gathering point in the common surface network, based on the shared EOS characterization and the initial EOS characterization of each reservoir;

determine whether or not the simulated fluid production for the gathering point includes mixed fluids from different reservoirs in the plurality of reservoirs;

when the simulated fluid production for the gathering point is determined not to include mixed fluids from different reservoirs, calculate first data representing properties of fluids to be produced at the gathering point using the initial EOS characterization for a corresponding one of the plurality of reservoirs;

when the simulated fluid production for the gathering point is determined to include mixed fluids from different reservoirs:

calculate second data representing properties of the mixed fluids to be produced at the gathering point using the shared EOS characterization of the plurality of reservoirs;

determine whether or not the second data matches the PVT data associated with each reservoir from which the mixed fluids are to be produced at the gathering point;

when the second data is determined not to match the PVT data, adjust the shared EOS characterization based on a difference between the second data and the PVT data; and repeat the calculation of the second data, the determination, and the adjustment functions with respect to the mixed fluids until the second data is determined to match the PVT data associated with the mixed fluids;

determine operating settings for a production well associated with each reservoir from which fluids are to be produced at the gathering point in the common surface network, based on at least one of the first data or the second data; and control, using control signals transmitted via a communication network to a wellsite control unit associated with the production well, production operations at the production well according to the determined operating settings.

10. The system of claim 9, wherein the PVT data is based on existing data within a range of temperature and pressure conditions within the common surface network.

11. The system of claim 9, wherein the initial EOS characterization for each reservoir includes a previously established EOS characterization for the fluids in that reservoir, and the PVT data is generated based on the previously established EOS characterization.

12. The system of claim 9, wherein the functions performed by the processor further include functions to define a common set of light components with identical EOS properties for use by all fluid characterizations.

13. The system of claim 12, wherein the functions performed by the processor further include functions to define a C7+ characterization for the fluids in each of the plurality of reservoirs.

14. The system of claim 13, wherein the functions performed by the processor further include functions to adjust a molecular weight of a C7+ fraction to match a saturation pressure thereof.

15. The system of claim 14, wherein the functions performed by the processor further include functions to individually match the PVT data for the fluids in each reservoir by adjusting the C7+ characterization of each fluid, without regard for common components.

16. The system of claim 15, wherein the functions performed by the processor further include functions to determine a common component set for the C7+ fraction and applying mixing rules to determine composition and properties of common components.

17. A non-transitory computer-readable storage medium having instructions stored therein, which when executed by a computer cause the computer to perform a plurality of functions, including functions to:

determine pressure-volume-temperature (PVT) data for fluids in each of a plurality of reservoirs coupled to a common surface network, based on an initial equation of state (EOS) characterization of the fluids in each reservoir, the initial EOS characterization for each reservoir including a set of light fluid components that are common across the plurality of reservoirs and at least one heavy fluid component that is unique to that reservoir;

generate a shared EOS characterization representing each of the fluids across the plurality of reservoirs, based on the corresponding PVT data for the fluids in each reservoir;

simulate fluid production from the plurality of reservoirs to a gathering point in the common surface network, based on the shared EOS characterization and the initial EOS characterization of each reservoir;

determine whether or not the simulated fluid production for the gathering point includes mixed fluids from different reservoirs in the plurality of reservoirs;

when the simulated fluid production for the gathering point is determined not to include mixed fluids from different reservoirs, calculate first data representing properties of fluids to be produced at the gathering point using the initial EOS characterization for a corresponding one of the plurality of reservoirs;

when the simulated fluid production for the gathering point is determined to include mixed fluids from different reservoirs:

calculate second data representing properties of the mixed fluids to be produced at the gathering point using the shared EOS characterization of the plurality of reservoirs;

determine whether or not the second data matches the PVT data associated with each reservoir from which the mixed fluids are to be produced at the gathering point;

when the second data is determined not to match the PVT data, adjust the shared EOS characterization based on a difference between the second data and the PVT data; and repeat the calculation of the second data, the determination, and the adjustment functions with respect to the mixed fluids until the second data is determined to match the PVT data associated with the mixed fluids;

determine operating settings for a production well associated with each reservoir from which fluids are to be produced at the gathering point in the common surface network, based on at least one of the first data or the second data; and control, using control signals transmitted via a communication network to a wellsite control unit associated with the production well, production operations at the production well according to the determined operating settings.

18. The non-transitory computer-readable storage medium of claim 17, wherein the PVT data is based on existing data within a range of temperature and pressure conditions within the common surface network.

19. The non-transitory computer-readable storage medium of claim 17, wherein the initial EOS characterization for each reservoir includes a previously established EOS characterization for the fluids in that reservoir, and the PVT data is generated based on the previously established EOS characterization.

20. The non-transitory computer-readable storage medium of claim 17, wherein the functions performed by the computer further include functions to define a common set of light components with identical EOS properties for use by all fluid characterizations.

* * * * *

UNITED STATES PATENT AND TRADEMARK OFFICE

CERTIFICATE OF CORRECTION

PATENT NO. : 10,400,548 B2
APPLICATION NO. : 15/116189
DATED : September 3, 2019
INVENTOR(S) : Terry Wong et al.

It is certified that error appears in the above-identified patent and that said Letters Patent is hereby corrected as shown below:

On the Title Page

Item (57), under ABSTRACT, Line 12: after “each reservoir” and before “the shared EOS”, delete “to”;

In the Specification

In Column 3, Line 31: delete “is”;

In Column 10, Line 39: delete “is”;

In Column 11, Line 12: delete “to” before the word ‘simulation’;

In Column 12, Line 1: delete “is”;

In Column 13, Line 26: delete “to”;

In Column 16, Line 4: “petrofacics” should be --petrofacies--

Signed and Sealed this
Fourteenth Day of January, 2020

Andrei Iancu
*Director of the United States Patent and Trademark Office*